United States Patent [19]

Clark et al.

[11] Patent Number: 4,696,302

[45] Date of Patent: Sep. 29, 1987

[54] PROCTOLOGIC DEVICE

[76] Inventors: Leigh B. Clark, R.F.D. Box 142, Del Mar, Calif. 92014; Larry Howell, 6939 Caminito Entrada, San Diego, Calif. 92119; Richard G. Hunter, 9129 Village Glen Dr., #275, San Diego, Calif. 92123

[21] Appl. No.: 764,106

[22] Filed: Aug. 9, 1985

[51] Int. Cl.[4] .............................. A61F 7/03; A61F 7/12
[52] U.S. Cl. ........................................ 128/401; 44/3.1;
126/263
[58] Field of Search ................ 128/401; 126/204, 263;
252/70; 44/3 A

[56] References Cited

U.S. PATENT DOCUMENTS

| | | | |
|---|---|---|---|
| 3,170,465 | 2/1965 | Henney et al. | 128/401 |
| 3,311,459 | 3/1967 | Francis et al. | 126/263 X |
| 3,643,665 | 2/1972 | Caillouette | 128/403 |
| 3,785,111 | 1/1974 | Pike | 53/14 |
| 3,804,077 | 4/1974 | Williams | 128/403 |
| 3,807,118 | 4/1974 | Pike | 53/14 |
| 3,874,504 | 4/1975 | Verakas | 206/219 |
| 3,939,842 | 2/1976 | Harris | 128/401 |
| 3,951,127 | 4/1976 | Watson | 126/206 |
| 4,067,313 | 1/1978 | Donnelly | 126/263 |
| 4,142,529 | 3/1979 | Latenser et al. | 128/401 |
| 4,227,535 | 10/1980 | Connor | 128/401 |
| 4,331,151 | 5/1982 | Golden | 128/401 |
| 4,402,402 | 9/1983 | Pike | 206/209 |

*Primary Examiner*—Anton O. Oechsle
*Attorney, Agent, or Firm*—Brown, Martin, Haller & Meador

[57] ABSTRACT

A device for self-administered treatment of hemorrhoids and other rectal disorders generally comprises an outer vessel including a hollow, thin-walled, flexible elongated tubular body portion having an inner closed end and an outer closed end and dimensioned for manual rectal insertion of the inner end, and having an enlarged stop portion at the outer end to prevent rectal insertion of the outer end and to insure proper positioning during use. The inner end has a portion of larger circumference to prevent expulsion of the device during use by anal spincter action. Chemical components within the outer vessel produce an exothermic reaction. An inner vessel, disposed within the outer vessel, contains at least one of the chemical components, and being facturable upon flexion of the outer vessel, provides for mixture of the chemicals. The device is intended for insertion into the anal canal to raise the temperature of the wall surface to approximately 45° C. In a preferred embodiment dissolution of a salt (calcium chloride) quickly raises the temperature of the device to the desired temperature and hydration of an oxide (calcium oxide) maintains this temperature. The hydation reaction is throttled by mixing the calcium oxide with a hydrophobic agent (lauric acid) and compressing the mixture, and by the presence of the dissolved ionic salt.

13 Claims, 2 Drawing Figures

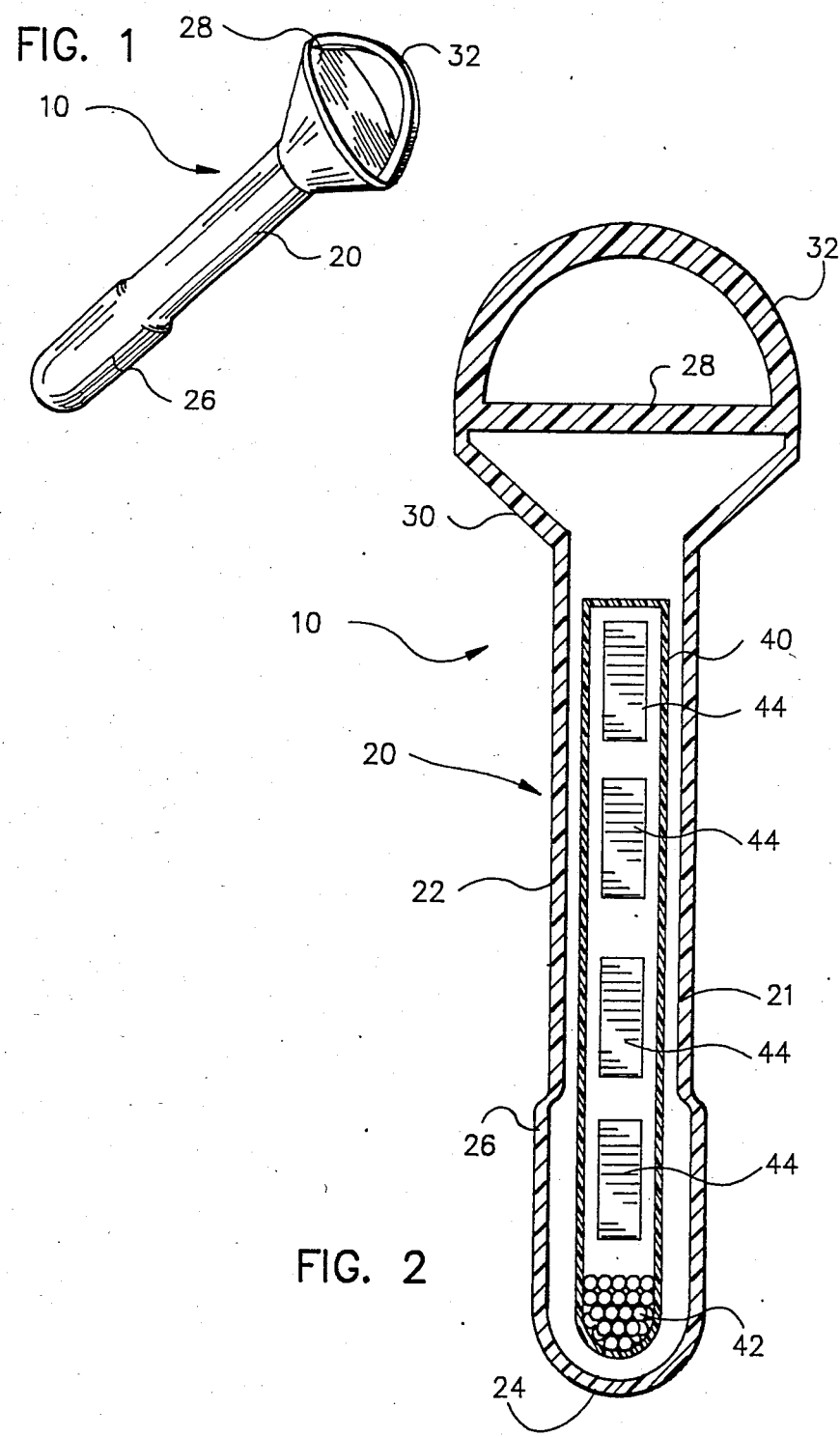

PROCTOLOGIC DEVICE

BACKGROUND OF THE INVENTION

1. Field of the Invention

This invention relates in general to devices for heating the anal canal for treating hemorrhoids and other rectal disorders and more specifically involves a device for insertion into the anal canal, the device containing chemicals for producing an exothermic reaction.

2. Background of the Invention

It has been recognized that hemorrhoids and other rectal disorders may be treated by heating. U.S. Pat. No. 4,142,529 of Latenser et al, incorporated herein by reference, described a process and device for therapeutically treating hemorrhoids. The proctologic device generally comprises an appliance for insertion into the anal canal thru the anus. The appliance has an elongated cylindrical body for intimately contacting the anal canal wall and has an electrical resistor heating element mounted internally; a source of electrical energy; an electrical cable between the source and appliance; and a temperature sensor and controlling apparatus. This electrical apparatus is bulky and expensive. The electronic device is relatively unsanitary and needs to be sanitized or sterilized between uses. These shortcomings restrict the use of such a device.

Therefore, it is desirable to have a device capable of heating the anal canal.

It is also desirable that such a device be inexpensive and disposable.

It is further desirable that such as device be small in size and not require an external power source and therefore can be used at almost any time and under many conditions.

SUMMARY OF THE INVENTION

According to the invention, a device for self-administered treatment of hemorrhoids and other rectal disorders comprises an outer vessel including a hollow, thin-walled, flexible, elongated tubular body portion having an inner closed end and an outer closed end, and dimensioned for manual rectal insertion of the inner end. An enlarged stop portion at the outer end prevents rectal insertion of the outer end and insures proper positioning during use. Within the outer vessel are chemical components for producing an exothermic reaction. An inner vessel, disposed within the outer vessel, containing at least one of the chemical components is fracturable upon flexion of the outer vessel and provides for mixture of the components to produce the exothermic reaction. The exothermic reaction is designed to quickly raise the temperature of the device to approximately 45° C. and maintain this temperature for approximately ten minutes during use in the anal canal.

In the exemplary embodiment, the initial rapid reaction includes the dissolution of a salt and the continued reaction includes the hydration of an oxide. In the preferred embodiment, the salt is calcium chloride and the oxide is calcium oxide. The continued exothermic reaction rate is partially controlled by mixing a hydrophobic material, lauric acid, with the calcium oxide and compressing the mixture into tablets at 25,000 psi. The ionic concentration of calcium from the instant rapid reaction serves to throttle the hydration reaction. Additionally, the depletion of water at the hydration reaction front tends to throttle the reaction.

The device is composed of non-toxic, biocompatible materials so as to be safe for the intended use.

The device is portable, inexpensive, and disposable.

Other features and many attendant advantages of the invention will become apparent upon a reading of the following detailed description together with the drawings, wherein like reference numerals refer to like parts throughout.

BRIEF DESCRIPTION OF THE DRAWINGS

FIG. 1 is a perspective view of a preferred embodiment of the invention.

FIG. 2 is an enlarged longitudinal sectional view of the device of FIG. 1.

DETAILED DESCRIPTION OF THE INVENTION

With reference to the drawings, and more particularly to FIG. 1 thereof, there is illustrated a perspective view of preferred embodiment of the device, shown generally as 10, for the treatment of hemorrhoids and other rectal disorders. As best seen in FIG. 2, the device 10 is comprised of an outer vessel 20 and inner vessel 40. The outer vessel 20 includes elongated tubular body portion 22 which is essentially a hollow, thin-wall tube dimensioned for intimate contact with the tissues of the anal canal and having an inner closed end 24 dimensioned for manual rectal insertion. The insertion end 24 of tubular body portion 22 includes a portion of slightly larger circumference 26 to prevent expulsion by anal spincter action. To obtain and maintain intimate contact with the anal canal tissues, including hemorrhoids, it is preferable that the tubular body porton 22 have a length of approximately 2.75 inches to extend totally from the anus through the anal canal to the rectum. Preferably the tubular body portion 22 has a diameter of approximately 0.56 inches in the spincter region and approximately 0.625 inches in the larger circumference portion 26 of the rectal area.

Outer vessel 20 includes an outer closed end 28 having an enlarged stop portion 30. Outer stop portion 30 is designed to prevent complete rectal insertion of the device and to insure proper positioning of the device 10 during use. A handle 32 may be integrally molded with the stop portion 30 or otherwise conventionally attached to the stop portion 30 to aid in handling, insertion and extraction of the device 10.

Preferably, the outer vessel 20 is molded of tissue-compatible, non-toxic material, such as polyethylene although other materials may also work. Low density polyethylene has been found to have the desirable biocompatibility, heat transfer characteristics, and flexibility necessary for the application of this invention.

Inner vessel 40 is dimensioned to fit in outer vessel 20. In the preferred embodiment, inner vessel 40 is tubular in shape with a length of 2.163 inches, an outside diameter of 0.407 inches and an inside diameter of 0.375 inches. In the preferred embodiment, chemicals within the inner vessels 40 are combined with water in the outer vessel 20 by rupturing the inner vessel through flexure of the outer vessel. In the preferred embodiment the inner vessel is fusion molded using polypropylene.

Inner vessel 40 contains approximately 1.2 grams 42 of anhydrous, calcium chloride ($CaCl_2$) and four tablets 44 of calcium oxide ($CaO$) and lauric acid [$CH_3(CH_2)_{10}COOH$]. To prepare the tablets 44, calcium oxide and lauric acid are ground together in the proportions four parts calcium oxide to 1 part lauric acid. This mixture of materials is then pressed at 25,000 psi onto cylindrical tablets. In the preferred embodiment, these cylindrical tablets are 0.4 inches long and 0.25 inches in diameter. Each tablet 44 has a mass of about 1.25 grams.

During assembly of the device 10 the inner vessel is filled with the above-indicated chemicals and sealed first with room-temperature vulcanizing silicone rubber (RTV) and then with a final coating of parafin. The inner vessel 40 is then placed into the outer vessel 20 which is filled with approximately 2 milliliters of water. The outer end 28 is then sealed, such as by ultrasonically welded polyethylene.

The device 10 is activated by squeezing or flexing the outer vessel 20 with enough force to rupture the inner vessel 40. After rupturing the inner vessel 40, the device 10 is properly activated by shaking to mix the chemicals. The device 10 is then inserted thru the anus into the anal canal.

The above-identified chemicals, combined, produce two major exothermic reactions. These include an initial rapid reaction for quickly raising the temperature of the device to near the desired 45° C. and a continued reaction for providing heat over a period of time to maintain a temperature of approximately 45° C. over that period of time.

The initial rapid reaction for quickly raising the device 10 to the desired temperature of approximately 45° C. includes dissolution of the salt calcium chloride, in water according to Formula 1.

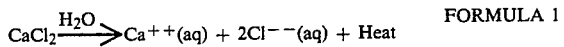

FORMULA 1

This reaction occurs very fast and quickly raises the temperature of the device near to the desired 45° C.

The heat generating continued chemical reaction is the hydration of calcium oxide as shown in Formula 2.

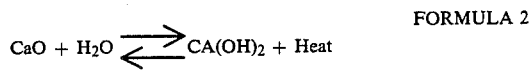

FORMULA 2

This exothermic reaction produces approximately 15.3 kilocalories per mole of calcium oxide. The hydration of calcium oxide by exothermic reaction, tends to progress exponentially, that is, the more heat produced, the faster the rate of heat production. In the preferred embodiment, this reaction is held in check to maintain the desired temperature by a combination of means: (1) the compaction of the calcium oxide makes it more dense and presents a smaller surface area for reaction; (2) the lauric acid is hydrophobic in nature and serves to prevent rapid wetting of the grains of calcium oxide, thereby substantially retarding the rate of the hydration reaction; and (3) the hydration of calcium oxide, which is a solid, produces calcium hydroxide, also a solid, therefore, as the reaction front moves within the tablet the front becomes more depleted of water, which consequently slows the reaction. Additionally, the ionic concentrations of calcium from the initial rapid reaction increasingly throttles the hydration reaction. Once the calcium chloride is dissolved (minimum concentration initially is about 4 molar) the solubility of the calcium hydroxide product in the aqueous phase is severely retarded.

As a result of the throttling methods, the rate of temperature increase is slow enough from rectal body temperature of 37.5° C. to approximately 45° C. to allow adaptation to the rise in temperature without producing pain. This rate is approximately 1° per 5 seconds or slower, a rate of rise known not to elicit pain. The above reactions quickly raise the temperature of the vessel to approximately 45° C. and are designed to maintain that temperature in the anal canal for greater than 10 minutes.

It is important to note that the chemical components of the device are non-toxic in both the reacted and unreacted states. The pH of the liquid phase in the reaction vessel is less than 10.9 units at all times. Therefore, the vessel and contents are designed so as to not impose a danger to the user.

The insertion portion of the device may be packaged pre-lubricated with a non-toxic and polymer-compatible lubricant or a lubricant may be added upon use. The lubricant may also contain a pharmaceutically active agent, such as a local anesthetic, antipruritic, anti-inflammatory, etc.

The tubular body portion 32 may be designed to dilate the anal spincter thereby aiding in elimination.

Because the device requires no external power source, it can be used at nearly any time and under many conditions. Additionally, it does not require an electrical power source which can short, malfunction, or otherwise harm the patient.

The materials comprising the device are inexpensive. This contributes to the attractiveness of its disposable nature. Being disposable, the device does not have to be cleaned after use and is therefore more sanitary than reusable devices.

The device may also have application as an aid in overcoming impotence.

The device may also be used for treatment of vaginal spasms which can prevent intercourse.

From the foregoing description it is seen that the present invention provides a safe and convenient manner of treating rectal-area disorders by lubricating the anal canal, by gently dilating the anal spincter, and by supplying controlled heat to the rectal area.

Although a particular embodiment of the invention has been illustrated and described, modification and changes will become apparent to those skilled in the art, and it is intended to cover in the appended claims, such modifications and changes as come within the true spirit and scope of the invention.

We claim:

1. A disposable device for self-administered heat treatment, comprising:
    an outer vessel dimensioned for manual rectal insertion comprising:
      a hollow, thin walled, flexible, elongated tubular body portion having a volume less than about 7 cubic centimeters; with an inner closed and, and an outer closed end;
    chemical means within said outer vessel including components for producing an exothermic reaction and for heating and maintaining said outer vessel at a temperature of about 45 degrees centigrade; at least a particular one of the components being mobile for mixture with other components to provide a thermal reaction between component;
    an inner vessel disposed within said outer vessel; said inner vessel containing at least one of said chemical components; said inner vessel being fracturable upon flexion of said outer vessel to provide for mixture of the mobile component with the other components;
said components comprising:
water;
a salt for quickly raising the device to a desired temperature through dissolution in said water;
an oxide for providing heat over a prolonged period through hydration with said water; and
a hydrophobic agent.

2. The device of claim 1 wherein said salt is calcium chloride.

3. The device of claim 1 wherein said oxide is calcium oxide.

4. The device of claim 1 wherein said hydrophobic agent is lauric acid.

5. A device for self-administered heat treatment of hemorrhoids, comprising:
an outer vessel comprising:
a hollow, thin walled, flexible, elongated tubular body portion;
an inner closed end; and
an outer closed end; said outer vessel dimensioned for manual rectal insertion of said inner end and having an enlarged stop portion at said outer end to prevent rectal insertion of said outer end and to insure proper positioning during treatment, and said inner end including a portion of larger circumference to prevent expulsion of the device during use by anal spincter action;
chemical means within said outer vessel including components for producing an exothermic reaction and for heating and maintaining said outer vessel at a predetermined temperature; at least a particular one of the components being mobile for mixture with other components to provide a thermal reaction between components; said components include:
initial rapid reaction means for quickly raising the temperature of the device to a desired temperature, including a salt and water;
continued reaction components for providing heat over a period of time, including an oxide and water; an inner vessel disposed within said outer vessel; said inner vessel containing at least one of said chemical components; said inner vessel being fracturable upon flexion of said outer vessel to provide for mixture of the mobile component with the other components; and
a hydrophobic agent mixed with said oxide to slow a reaction of said oxide with water.

6. The device of claim 5 wherein said hydrophobic agent is lauric acid.

7. The device of claim 6 wherein said calcium oxide and said lauric acid are mixed approximately 4 parts of calcium oxide and one part lauric acid and are compressed to form a tablet.

8. The device of claim 7 wherein said tablet is compressed to approximately 25,000 psi.

9. The device of claim 7 wherein said chemical components have approximately the following ratios:
4 grams calcium oxide to one gram lauric acid to 1.2 grams calcium chloride to 2 grams water.

10. The device of claim 1 further comprising a handle having an arcuate member with two ends, said ends being joined to said enlarged stop portion.

11. A device for self-administered heat treatment, comprising:

an outer vessel including a hollow, thin walled, flexible, elongated tubular body portion with inner and an outer closed ends;
said outer vessel dimensioned for manual rectal insertion of said inner end and having an enlarged stop portion at said outer end to prevent rectal insertion of said outer end and to insure proper positioning during use;
chemical means within said outer vessel including components for producing an exothermic reaction; at least a particular one of the components being mobile for mixture with other components to provide a thermal reaction between components, said components comprising:
initial rapid reaction means for quickly raising the device to a desired temperature;
continued reaction means for providing heat over a prolonged period comprising an oxide and water and said continued reaction means involves hydration of said oxide; and
temperature maintenance means for controlling the rate of reaction of said continued reaction and for maintaining the desired temperature comprising lauric acid mixed with said oxide for slowing said hydration of the oxide;
an inner vessel disposed within said outer vessel; said inner vessel containing at least one of said chemical components; said inner vessel being fracturable upon flexion of said outer vessel to provide for mixture of the mobile component with the other components.

12. A device for self-administered heat treatment, comprising:
an outer vessel including a hollow, thin walled, flexible, elongated tubular body portion with inner and an outer closed ends;
said outer vessel dimensioned for manual rectal insertion of said inner end and having an enlarged stop portion at said outer end to prevent rectal insertion of said outer end and to insure proper positioning during use;
chemical means within said outer vessel including components for producing an exothermic reaction; at least a particular one of the components being mobile for mixture with other components to provide a thermal reaction between components, said components comprising:
initial rapid reaction means for quickly raising the device to a desired temperature comprising calcium chloride; and wherein said initial rapid reaction means comprises dissolution of said calcium chloride;
continued reaction means for providing heat over a prolonged period comprising an oxide and water and said continued reaction means involves hydration of said oxide; and
temperature maintenance means for controlling the rate of reaction of said continued reaction and for maintaining the desired temperature and wherein said temperature maintenance means comprises the presence of the ionic state of said salt and lauric acid mixed with said oxide for slowing said continuing reaction means; and
an inner vessel disposed within said outer vessel; said inner vessel containing at least one of said chemical components; said inner vessel being fracturable upon flexion of said outer vessel to provide for mixture of the mobile component with the other components.

13. A device for self-administered heat treatment of hemorrhoids, comprising:
an outer vessel comprising:
a hollow, thin walled, flexible, elongated tubular body portion;
an inner closed end; and
an outer closed end; said outer vessel dimensioned for manual rectal insertion of said inner end and having an enlarged stop portion at said outer end to prevent rectal insertion of said outer end and to insure proper positioning during treatment, and said inner end including a portion of larger circumference to prevent expulsion of the device during use by anal spincter action;
chemical means within said outer vessel including components for producing an exothermic reaction; at least a particular one of the components being mobile for mixture with other components to provide a thermal reaction between components; said components include:
initial rapid reaction means for quickly raising the temperature of the device to a desired temperature, including a salt and water;
continued reaction components for providing heat over a period of time, including calcium oxide and water; and
temperature maintenance means for controlling the rate of reaction of said continued reaction and for maintaining the desired temperature and wherein said temperature maintenance means comprises the presence of the ionic state of said salt and lauric acid mixed with said calcium oxide; and
an inner vessel disposed within said outer vessel; said inner vessel containing at least one of said chemical components; said inner vessel being fracturable upon flexion of said outer vessel to provide for mixture of the mobile component with the other components.

* * * * *

UNITED STATES PATENT AND TRADEMARK OFFICE
CERTIFICATE OF CORRECTION

PATENT NO. : 4,696,302

DATED : September 29, 1987

INVENTOR(S) : Clark et al.

It is certified that error appears in the above-identified patent and that said Letters Patent is hereby corrected as shown below:

Column 4, claim 1, line 55, "and", first occurrence should read

-- end --.

Signed and Sealed this

Tenth Day of May, 1988

Attest:

DONALD J. QUIGG

Attesting Officer

Commissioner of Patents and Trademarks